US010645965B2

(12) United States Patent
O'Hara (10) Patent No.: US 10,645,965 B2
(45) Date of Patent: May 12, 2020

(54) DIETARY COMPOSITION WITH PROBIOTICS AND PREBIOTICS

(71) Applicant: Optibiotix Limited, Heslington (GB)

(72) Inventor: Stephen Patrick O'Hara, York (GB)

(73) Assignee: OPTIBIOTIX LIMITED, Heslington, York (GB)

( * ) Notice: Subject to any disclaimer, the term of this patent is extended or adjusted under 35 U.S.C. 154(b) by 0 days.

(21) Appl. No.: 15/524,739

(22) PCT Filed: Nov. 5, 2015

(86) PCT No.: PCT/GB2015/053350
§ 371 (c)(1),
(2) Date: May 5, 2017

(87) PCT Pub. No.: WO2016/071693
PCT Pub. Date: May 12, 2016

(65) Prior Publication Data
US 2017/0318851 A1 Nov. 9, 2017

(30) Foreign Application Priority Data

| Nov. 5, 2014 | (WO) | ................ PCT/GB2014/053288 |
| Feb. 12, 2015 | (GB) | .................................. 1502355.9 |

(51) Int. Cl.
| A23L 33/135 | (2016.01) |
| A61K 31/702 | (2006.01) |
| A61K 31/733 | (2006.01) |
| A61K 31/736 | (2006.01) |
| A61K 35/741 | (2015.01) |
| A23L 29/244 | (2016.01) |
| A23L 33/00 | (2016.01) |
| A23L 33/15 | (2016.01) |
| A23L 33/16 | (2016.01) |
| A61K 45/06 | (2006.01) |
| A23L 33/21 | (2016.01) |
| A61K 33/24 | (2019.01) |
| A61K 9/48 | (2006.01) |
| A23C 9/123 | (2006.01) |
| A23C 9/13 | (2006.01) |
| A23C 9/133 | (2006.01) |
| A23C 9/137 | (2006.01) |
| A23C 17/02 | (2006.01) |
| A23C 19/06 | (2006.01) |

(Continued)

(52) U.S. Cl.
CPC .......... *A23L 33/135* (2016.08); *A23C 9/1238* (2013.01); *A23C 9/133* (2013.01); *A23C 9/137* (2013.01); *A23C 9/1307* (2013.01); *A23C 9/1322* (2013.01); *A23C 17/02* (2013.01); *A23C 19/062* (2013.01); *A23L 29/244* (2016.08); *A23L 33/15* (2016.08); *A23L 33/16* (2016.08); *A23L 33/21* (2016.08); *A23L 33/30* (2016.08); *A23L 33/40* (2016.08); *A61K 9/48* (2013.01); *A61K 31/702* (2013.01); *A61K 31/733* (2013.01); *A61K 31/736* (2013.01); *A61K 33/24* (2013.01); *A61K 35/741* (2013.01); *A61K 35/744* (2013.01); *A61K 35/747* (2013.01); *A61K 45/06* (2013.01); *A23V 2002/00* (2013.01); *A23Y 2220/15* (2013.01); *A23Y 2220/29* (2013.01); *A23Y 2240/75* (2013.01); *A61K 2035/115* (2013.01)

(58) Field of Classification Search
None
See application file for complete search history.

(56) References Cited

U.S. PATENT DOCUMENTS 9,320,769 B2 * 4/2016 Sun ...................... A61K 36/258

FOREIGN PATENT DOCUMENTS

| CN | 101438738 A | 5/2009 |
| DE | 202012101011 U1 | 5/2012 |

(Continued)

OTHER PUBLICATIONS

Abdollahi et al., "Effect of Chromium on Glucose and Lipid Profiles in Patients with Type 2 Diabetes; A Meta-analysis Review of Randomized Trials." Journal of Pharmacy & Pharmaceutical Sciences, vol. 16, No. 1, pp. 99-114, 2013.

(Continued)

*Primary Examiner* — Vera Afremova
(74) *Attorney, Agent, or Firm* — Denise L. Mayfield; Dykema Gossett PLLC (57) ABSTRACT

The present invention relates to compositions for use and formulation as weight management products and in particular fermented dairy foodstuffs. The compositions generally comprise two or more of the following components: a) a microbiome modifying component; b) a satiety modifying component; and c) a metabolic modifying 5 component and at least one of the following: d) *Streptococcus thermophilus* CBS 139100 and *Lactobacillus delbrueckii* subsp. *bulgaricus* CBS 139099 microbial strains or mutant strains or fragments or fractions thereof; e) a combination of *Streptococcus thermophilus* and *Lactobacillus delbrueckii* subsp. *bulgaricus* microbial strains which together, or individually, are capable of secreting polysaccharides having high levels of galactosamine 10 and no or low levels of rhamnose and glucuronic acid when grown on a dairy substrate; or f) polysaccharides formed of: i) 15-25% galactosamine; ii) 45-60% galactose; and iii) 20-30% glucose. The compositions may also be useful in the management or treatment of obesity, elevated cholesterol, diabetes, hypertension or heart disease.

18 Claims, 3 Drawing Sheets

(51) Int. Cl.
A61K 35/744 (2015.01)
A61K 35/747 (2015.01)
A61K 35/00 (2006.01)

(56) References Cited

FOREIGN PATENT DOCUMENTS

DE 202014103285 U1 10/2014
KR 1020130079173 A 7/2013

OTHER PUBLICATIONS

Archer et al., "Effect of fat replacement by inulin or lupin-kernel fibre on sausage patty acceptability, post-meal perceptions of satiety and food intake in men†." British Journal of Nutrition, vol. 91, pp. 591-599, 2004.
Bates et al., "National Diet and Nutrition Survey. Headline results from Years 1 and 2 (combined) of the Rolling Programme." Food Standards Agency & Department of Health, London, pp. 1-68, 2008/2009-2009/2010.
Cani et al., "Dietary non-digestible carbohydrates promote L-cell differentiation in the proximal colon of rats." British Journal of Nutrition, vol. 98, pp. 32-37, 2007.
Cani et al., "Gut microbiota fermentation of prebiotics increases satietogenic and incretin gut peptide production with consequences for appetite sensation and glucose response after a meal 1-3." American Journal of Clinical Nutrition, vol. 90, pp. 1236-1243, 2009.
Cani et al., "Oligofructose promotes satiety in healthy human: a pilot study." European Journal of Clinical Nutrition, vol. 60, pp. 567-572, 2006.
Chua et al., "Traditional uses and potential health benefits of Amorphophallus konjac K. Koch ex N.E.Br." Journal of Ethnopharmacology, vol. 128, pp. 268-278, 2010.
Delzenne et al., "Impact of inulin and oligofructose on gastrointestinal peptides." British Journal of Nutrition, vol. 93, Suppl. 1, pp. S157-S161, 2005.
Genta et al., "Yacon syrup: Beneficial effects on obesity and insulin resistance in humans" Clinical Nutrition, vol. 28, pp. 182-187, 2009.
Habib et al., "Co-localisation and secretion of glucagon-like peptide 1 and peptide YY from primary cultured human L cells." Diabetologia, vol. 56, pp. 1413-1416, 2013.
Overduin et al., "Role of the Duodenum and Macronutrient Type in Ghrelin Regulation." Endodrinology, vol. 146, No. 2, pp. 845-850, 2005.
Parnell et al., "Weight loss during oligofructose supplementation is associated with decreased ghrelin and increased peptide YY in overweight and obese adults 2." The American Journal of Clinical Nutrition, vol. 89, No. 6, pp. 1751-1759, 2009.
Peters et al., "No effect of added b-glucan or of fructooligosaccharide on appetite or energy intake 1-3." The American Journal of Clinical Nutrition, vol. 89, pp. 58-63, 2009.
Pittler et al., "Chromium picolinate for reducing body weight: Meta-analysis of randomized trials." International Journal of Obesity, vol. 27, pp. 522-529, 2003.
Salas-Salvado et al., "Effect of two doses of a mixture of soluble fibres on body weight and metabolic variables in overweight or obese patients: a randomised trial." British Journal of Nutrition, vol. 99, pp. 1380-1387, 2008.
Sood et al, "Effect of glucomannan on plasma lipid and glucose concentrations, body weight, and blood pressure: systematic review and meta-analysis 1,2." The American Journal of Clinical Nutrition, vol. 88, pp. 1167-1175, 2008.
Verhoef et al., "Effects of oligofructose on appetite profile, glucagon-like peptide 1 and peptide YY3-36 concentrations and energy intake." British Journal of Nutrition, vol. 106, pp. 1757-1762, 2011.
Vuksan et al., "Beneficial Effects of Viscous Dietary Fiber From Konjac-Mannan in Subjects With the Insulin Resistance Syndrome: Results of a controlled metabolic trial." Diabetes Care, vol. 23, No. 1, pp. 9-14, Jan. 2000.
Vuksan et al., "Viscosity rather than quantity of dietary fibre predicts cholesterol-lowering effect in healthy individuals." British Journal of Nutrition, vol. 106, pp. 1349-1352, 2011.
Yazaki et al., "A Pilot Study of Chromium Picolinate for Weight Loss" The Journal of Alternative and Complementary Medicine, vol. 16, No. 3, pp. 291-299, 2010.
Yoshida et al., "Effect of plant sterols and glucomannan on lipids in individuals with and without type II diabetes." European Journal of Clinical Nutrition, vol. 60, pp. 529-537, 2006.
Vaningelgem et al., "Biodiversity of Exopolysaccharides Produced by *Streptococcus thermophilus* Strains Is Reflected in Their Production and Their Molecular and Functional Characteristics." Applied and Environmental Microbiology, vol. 70, No. 2, pp. 900-912, Feb. 2004.
European Food Safety Authority, EFSA, "Statement of the Scientific Panel on Dietetic Products, Nutrition and Allergies on a request from the Commission related to dietary fibre." The EFSA Journal, pp. 1-8, Aug. 23, 2007. [Retrieved at http://www.efsa.europa.eu/en/efsajournal/doc/1060.pdf on Jan. 28, 2015].
International Search Report and Written Opinion for PCT/GB2015/053350 dated Feb. 1, 2016.

* cited by examiner

DIETARY COMPOSITION WITH PROBIOTICS AND PREBIOTICS

TECHNICAL FIELD OF THE INVENTION

The invention relates to food compositions for weight management.

BACKGROUND TO THE INVENTION

Overweight and obese are conditions defined as abnormal or excessive fat accumulation that may impair health. It results from imbalances in the body's regulation of energy intake, expenditure and storage.

Obesity is one of the greatest public health challenges of the 21st century. It is a complex condition, one with serious social and psychological dimensions, that affects virtually all age and socioeconomic groups in both developed and developing countries. The health consequences of obesity range from increased risk of premature death to serious chronic conditions that reduce the overall quality of life. Excess weight is the fifth leading risk for global deaths. At least 2.8 million adults die each year as a result of being overweight or obese. In addition, 44% of the diabetes burden, 23% of the ischaemic heart disease burden and between 7% and 41% of certain cancer burdens are attributable to being overweight or obese.

Among the reasons that have led to the dramatic increase in obesity are an increase in the intake of high fat, salt and refined sugar foods that are energy rich but otherwise low in nutritional value (vitamins, minerals, micronutrients) in combination with an increasingly sedentary nature to everyday life with a dramatic decrease in physical activity.

Prebiotics have attracted interests as candidate compounds for the control of obesity and associated metabolic disorders. In animal studies, prebiotics have been shown to regulate the intake of food, prevent weight gain, beneficially alter lipid metabolism and reduce obesity-related inflammation. So far, most studies have focused on simply supplementing the diet with inulin and fructooligosaccharides (FOS).

Prebiotics are dietary ingredients which can selectively enhance beneficial indigenous gut microbiota, such as lactobacilli or bifidobacteria, and are finding much increased application into the food sector. Prebiotics are non-digestible food ingredients that are selectively metabolised by colonic bacteria which contribute to improved health. As such, their use can promote beneficial changes within the indigenous gut microbial milieu and they can therefore help survivability of probiotics. They are distinct from most dietary fibres like pectin, celluloses, xylan, which are not selectively metabolised in the gut. Criteria for classification as a prebiotic is that it must resist gastric acidity, hydrolysis by mammalian enzymes and gastrointestinal absorption, it is fermented by intestinal microflora and selectively stimulates the growth and/or activity of intestinal bacteria associated with health and well-being.

One of the primary functions of the colonic microbiota is to salvage energy from dietary material that has not been digested in the upper gastrointestinal tract, through participating in the initial hydrolysis of complex macromolecules, breaking them down into smaller fragments that can be utilised by other members of the gut microbiota. It is postulated that about 7% to 10% of the total daily energy requirements of the host are derived from colonic bacterial fermentation. In the absence of microbial fermentation in the gut, this energy contribution to would be lost to the host, as humans lack the enzymes necessary to catabolise plant polysaccharides and they would be excreted from the organism as waste. As such, it appears that the presence of a gut microbiota may lead to a direct increase in energy salvaging through the fermentation of dietary polysaccharides.

Although obesity is caused by an excess caloric intake which is not matched by an increase in energy expenditure, differences in gut microbiota composition and activities between individuals may also be an important contributing factor affecting energy homeostasis. This would imply that the gut microbiota of obese individuals would be more efficient in salvaging and/or storing energy from a specific diet compared to the microbiota of lean individuals.

Some dietary fibres can form viscous gels on exposure to an aqueous environment and their gelling properties may account for weight loss promoting effects by delaying gastric emptying, slowing bowel transit time and blunting post-prandial surges in insulin and glucose.

The texture of yoghurt may be modified by using strains of lactic acid bacteria which produce exopolysaccharides. Exopolysaccharides can increase the viscosity, thickness, stability and gel firmness of fermented milk products, including yoghurt. Exopolysaccharides may increase the viscosity of fermented milk products by interacting with milk proteins. The production of exopolysaccharides by the lactic acid culture can reduce the need for bio-thickeners or additional fat to increase the viscosity of the fermented milk product. Hydrocolloids of plant origin have been used to stabilise the gel structure of yoghurt. Many of these hydrocolloids are chemically modified or extracted using various chemicals. As their use is restricted in some countries, there is a need to identify alternative texture modulating agents.

Consumers increasingly demand products with reduced fat and/or sugar content and minimal additives. Using bacterial strains which secrete the desired exopolysaccharides reduces the need to add additional fat to increase the viscosity of fermented milk products. Exopolysaccharide producing strains also reduce the need to add additional sugar, stabilisers and thickeners. As less additional ingredients are needed to achieve desirable sensory characteristics production costs can be reduced.

There is also motivation to increase the viscosity of food products to increase satiation for consumers. Increased satiation can aid those on calorie controlled diets. Food products with a thicker texture may also have a slower transit through the gastrointestinal tract so prolonging the feeling of satiation. Furthermore, food products which also form complexes or impede digestion of food products during digestive transit are also believed to increase the feeling of satiation. Satiation is an important element for controlling food intake and can be used in weight management to discourage eating too much food and/or too regularly.

A food product with a thicker texture may also be useful for the suspension or incorporation of additional ingredients throughout the food product. This is often hard to achieve with food with low viscosity consistency or low fat content.

Many studies have shown that the amount and properties of the exopolysaccharides secreted by bacteria are strain dependent. Exopolysaccharides derived from *Lactobacillus delbrueckii* subsp. *bulgaricus* and *Streptococcus thermophilus* have shown large variation in composition, charge, spatial arrangement, rigidity and ability to interact with proteins. No defining correlation between exopolysaccharide concentration and viscosity of the food product has yet been established.

It is an object of the present invention to provide a formulation which can be used for weight management— whether included as a food stuff or added to food. It is a further object of the present invention to provide a formulation whose components have a synergistic effect on an individual so as to reduce or modulate weight gain. It would be preferably if such a formulation was effective in more than one area of weight management, for example modifying metabolism of fat and reducing energy gain by colonic bacterial fermentation. It would further be preferable to provide a formulation which enhances satiation. It would also be preferable that the formulation could be easily consumed as either a manufactured foodstuff or an additive which could be added to foods.

SUMMARY OF THE INVENTION

In accordance with a first aspect of the present invention, there is provided a composition comprising two or more of the following components:
 a) a microbiome modifying component;
 b) a satiety modifying component; and
 c) a metabolic modifying component,
and at least one of the following:
 d) *Streptococcus thermophilus* CBS 139100 and *Lactobacillus delbrueckii* subsp. *bulgaricus* CBS 139099 microbial strains or mutant strains or fragments or fractions thereof;
 e) a combination of *Streptococcus thermophilus* and *Lactobacillus delbrueckii* subsp. *bulgaricus* microbial strains which together, or individually, are capable of secreting polysaccharides having high levels of galactosamine and no or low levels of rhamnose and glucuronic acid when grown on a dairy substrate; or
 f) polysaccharides formed of:
  i. 15-25% galactosamine;
  ii. 45-60% galactose; and
  iii. 20-30% glucose.

If the composition comprises d) or e) then it may further comprise polysaccharides having high levels of galactosamine and no or low levels of rhamnose and glucuronic acid. If the composition comprises d) or e) then the microbial strains secrete polysaccharides comprising in the range of 45-60% galactose, 20-30% glucose and 15-25% galactosamine, based on the total weight of secreted exopolysaccharides. If the composition comprises e) or f) and further comprise *Streptococcus thermophilus* CBS 139100 and *Lactobacillus delbrueckii* subsp. *bulgaricus* CBS 139099 microbial strains, or mutant strains thereof.

Preferably, the composition comprises all of the components a) to c).

The term "dairy substrate" is intended to mean a food material which contains at least some milk solids.

The term "mutant strain" within the scope of this application is intended to mean any strains which are directly derived from those strains disclosed, but which are phenotypically different due to the introduction of one or more genetic mutations (whether by genetic engineering or selection).

The *Streptococcus thermophilus* and *Lactobacillus delbrueckii* subsp. *bulgaricus* microbial strains of d) and e) will preferably secrete polysaccharides comprising up to 25% galactosamine, up to 60% galactose and/or up to 30% glucose based on the total weight of secreted exopolysaccharides. More preferably, the microbial strains may secrete polysaccharides comprising up to 23% galactosamine, up to 55% galactose and/or up to 28% glucose based on the total weight of secreted exopolysaccharides. Most preferably, the microbial strains secrete polysaccharides comprising up to about 22% galactosamine, up to about 52% galactose and/or up to about 26% glucose based on the total weight of secreted exopolysaccharides.

Alternatively, the *Streptococcus thermophilus* and *Lactobacillus delbrueckii* subsp. *bulgaricus* microbial strains of d) and e) will preferably secrete polysaccharides comprising in the range of 15-25% galactosamine, 45-60% galactose and/or 20-30% glucose based on the total weight of secreted exopolysaccharides. More preferably, the microbial strains secrete polysaccharides comprising in the range of 20-23% galactosamine, 50-55% galactose and/or 23-28% glucose based on the total weight of secreted exopolysaccharides. Most preferably, the microbial strains secrete polysaccharides comprising about 22% galactosamine, about 52% galactose and/or about 26% glucose based on the total weight of secreted exopolysaccharides.

Preferably, the polysaccharides of f) comprise up to 25% galactosamine, up to 60% galactose and/or up to 30% glucose. More preferably, the food stabilising and/or thickening composition may comprise up to 23% galactosamine, up to 55% galactose and/or up to 28% glucose. Most preferably, the food stabilising and/or thickening composition will comprise up to about 22% galactosamine, up to about 52% galactose and/or up to about 26% glucose.

Preferably, the polysaccharides of f) comprises 20-23% galactosamine, 50-55% galactose and/or 23-28% glucose and/or 0-1% mannose. More preferably, the food stabilising composition comprises about 22% galactosamine, about 52% galactose and/or about 26% glucose.

If the composition comprises f) then it may further comprise *Streptococcus thermophilus* and *Lactobacillus delbrueckii* subsp. *bulgaricus* microbial strains or fragments or fractions thereof. Such strains will preferably comprise *Streptococcus thermophilus* CBS 139100 and *Lactobacillus delbrueckii* subsp. *bulgaricus* CBS 139099 microbial strains, or mutant strains thereof.

The microbiome modifying component may further comprise one or more additional microbial strains. Such additional microbial strains could be bacterial and fall within the scope of what is typically considered to be a "probiotic". The skilled addressee will also recognise that *Streptococcus thermophilus* and *Lactobacillus delbrueckii* subsp. *bulgaricus* are also generally understood to be "probiotic" bacteria. However, additional strains and/or species of probiotics may also be utilised within the composition. The microbiome modifying component may comprise or further comprise a growth medium for at least one or more of the desired microbial strains—these strains could already be present in the individual or included as part of the composition.

The microbiome modifying component may also comprise a selective microbial growth inhibitor and/or microbial cidal compound. Therefore the microbial strains which are already present in the individual may be manipulated by encouraging growth, inhibiting growth or actively killed. Such manipulation allows to the desired microbial population to be selected so as to provide their associated health benefits.

The microbiome modifying component preferably further comprises a prebiotic. If desired, the prebiotic may be producible by the probiotic bacterial strain by reverse enzyme reaction. The satiety modifying component preferably acts mechanistically to suppress appetite. The metabolic modifying component preferably acts to increase metabolism and/or modify insulin sensitivity.

The satiety modifying component may comprise dietary fibre and the metabolic modifying component may comprise chromium.

The term "dietary fibre" is intended to mean indigestible portions of food derived from plants which comprise soluble and insoluble fibres.

The term "chromium" covers all dietary chromium, including trivalent chromium (Cr(III) or $Cr^{3+}$) which naturally occurs in trace amounts in foods and water in addition to chromium chloride. Chromium acts systemically potentiating insulin action, increasing metabolic rate, influencing carbohydrate, lipid and protein metabolism and maintaining glucose levels.

The term "prebiotic" is intended to mean a selectively fermented ingredient that allows specific changes, both in the composition and/or activity in the gastrointestinal microflora flora that confers benefits upon host wellbeing and health. Prebiotics act in the colon and produce changes in the microbial flora which affect energy metabolism and gut peptides involved in satiation (GLP1, GLP2). These have a long acting affect.

Preferably, the dietary fibre comprises glucomannan. Gucomannam acts primarily in the stomach by suppressing appetite by gel formation in the stomach, causing distension and activating mechanoreceptors that signal increased satiety and fullness.

Preferably the prebiotic comprises one or more selected from: inulin, fructooligosaccharides (FOS), galactooligosaccharides (GOS), α-gluco-oligosaccharides, a low gas producing prebiotic and combinations thereof.

The dietary fibre may be present in an amount sufficient to provide a daily dose in the range of 0.5 to 15 g. The dietary dose may be in the range of 1 g to 3 g per day. More preferably, the dietary dose may be in the range of 1.5 g to 2.5 g per day. The chromium may be present in an amount sufficient to provide a daily dose in the range of 50 to 1000 μg. The chromium may be in a dose in the range of 100 to 750 μg per day. More preferably, the chromium may be in a dose in the range of 200 to 500 μg per day.

The prebiotic may be present in an amount sufficient to provide a daily dose in the range of 3 to 30 g. The prebiotic may be in a dose of 5 to 25 g per day. More preferably, the prebiotic may be in a dose of 10 to 20 g per day.

The composition may comprise a combination of:
a) glucomannan and chromium;
b) glucomannan, FOS and chromium;
c) glucomannan and FOS; or
d) glucomannan and a low gas producing prebiotic.

It will be apparent to the skilled addressee that the composition may be in any easily digestible form of a foodstuff or food additive. The composition could be used as a dietary supplement—for example to be blended with foods/drinks or consumed alongside foods/drinks. The composition may be grown on a dairy substrate and/or is formed as part of a dairy substrate or product or is used as a feedstock, ingredient or additive for use with a fermented or fermentable dairy foodstuff. Preferably, the composition may be formulated as a fermented or fermentable dairy foodstuff, such as yoghurt. The fermented or fermentable dairy foodstuff may be selected from one or more of the following: yoghurt, cheese, crème fraiche, sour cream, buttermilk, kefir, *acidophilus* milk, koumiss, filmjölk and viili. The fermented dairy foodstuffs may comprise fermented milk drinks used as prebiotics or probiotics.

Alternatively, the composition may be formulated as an additive, ingredient or starter culture for fermented or fermentable dairy foodstuffs The composition may further comprise one or more ingredients selected from: sweeteners, stabilisers, acidity regulators, water, flavourings, fats, emulsifiers, plant and/or vegetable extracts, vitamins, minerals, phytochemicals, antioxidants, and combinations thereof.

Sweeteners such as sugar, aspartame, fructose, glucose-fructose syrup and combinations thereof may be employed.

Stabilisers such as alginate, carrageenan, gelatin, guar gum, locust bean gum, pectin, modified maize starch, maltodextrin, starch and combinations thereof can be utilised. However, it should be noted that the combination of *Streptococcus thermophilus* CBS 139100 and *Lactobacillus delbrueckii* subsp. *bulgaricus* CBS 139099 microbial strains have been advantageously been found to confer superior gel-like properties to foodstuffs. The gel-like properties have been demonstrated to not only increase viscosity of liquids, but also maintain smoothness of the liquids over time. This has been found to be particularly advantageous for fermented or fermentable milk products such as yoghurts. It is believed that the improved gel-like properties are a result of the secretion (or indeed lack of secretion) of certain exopolysaccharides. As mentioned earlier, exopolysaccharides can increase the viscosity, thickness, stability and gel firmness of fermented milk products, such as yoghurt and exopolysaccharides may increase the viscosity of fermented milk products by interacting with milk proteins. The production of exopolysaccharides by the strains of this invention reduce the need for bio-thickeners or additional fat to increase the viscosity of the fermented milk product. It has been found that these particular strains produce greater amounts of galactosamine, galactose and glucose as opposed to other strains which produce greater amounts of rhamnose, mannose and glucuronic. It follows that if the composition is formulated in the form of a liquid, commonly used stabilisers can be included in smaller quantities or removed all together if desired by the use of the strains included in the composition of the present invention. Furthermore, low-fat formulations can also be prepared as the higher fat content is no longer required to increase viscosity.

It will be noted that in place of the strains, a mixture of the polysaccharides secreted by the microbial strains may be used in conjunction with the invention so as to contribute to the gel-like properties and increased viscosity. Additional components such as surfactants (or indeed fragments, fractions or components of the microbial strains) may be utilised in the composition to replace the physical and other properties that the strains themselves should only the exopolysaccharides be used independently.

It may be desirable to use acidity regulators such as citric acid, sodium citrate, calcium citrates and combinations thereof.

Additional ingredients such as water, flavourings, cocoa powder, fruit, coconut milk and combinations thereof may also be added.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B1, riboflavoin or B25 niacin or B3, pyridoxine or B6, folic acid or B9, cyanocobalimin or B12, pantothenic acid, biotin), and combinations thereof.

Minerals may include, but are not limited to, sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to carotenoids, chlorophyll, chlorophyllin, fiber, flavanoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

A composition may comprise:
a) 50 to 90% fermented or fermentable dairy food stuff comprising and/or fermented using *Streptococcus thermophilus* CBS 139100 and *Lactobacillus delbrueckii* subsp. *bulgaricus* CBS 139099;
b) 1 to 10% sweetener;
c) 5 to 20% GOS;
d) up to 1.5% glucomannan;
e) up to 0.010% chromium chloride; and optionally
f) 5 to 30% fruit preparation.

Preferably, the composition comprises 0.2 to 1.5% glucomannan and 0.005 to 0.010% chromium chloride.

The composition will preferably be used for weight management (including reducing overall mass) in an individual. The composition could be used in accordance with a prescribed diet plan or as a supplement or replacement of certain food components of an individual's diet. Furthermore, the composition could be formulated in a range of different products so that it can be consumed in a predetermined regime.

The composition may be for use in the treatment or management of obesity, elevated cholesterol, diabetes, hypertension or heart disease.

The following aspects of the present invention relate to methods of producing compositions as herein above described.

In one such further aspect, there is provided a method of producing a composition comprising providing two or more of the following components:
a) a microbiome modifying component;
b) a satiety modifying component; and
c) a metabolic modifying component,
and at least one of the following:
d) *Streptococcus thermophilus* CBS 139100 and *Lactobacillus delbrueckii* subsp. *bulgaricus* CBS 139099 microbial strains or mutant strains or fragments or fractions thereof;
e) a combination of *Streptococcus thermophilus* and *Lactobacillus delbrueckii* subsp. *bulgaricus* microbial strains which together, or individually, are capable of secreting polysaccharides having high levels of galactosamine and no or low levels of rhamnose and glucuronic acid when grown on a dairy substrate; or
f) polysaccharides formed of:
   i. 15-25% galactosamine;
   ii. 45-60% galactose; and
   iii. 20-30% glucose
and mixing the chosen components from a) to c) together with either d), e) or f) so as to form a mixture.

In accordance with a further such aspect, there is provided a method of producing a dairy product comprising the steps:
a) fermenting an initial dairy substrate using a culture comprising:
   i. *Streptococcus thermophilus* CBS 139100 and *Lactobacillus delbrueckii* subsp. *bulgaricus* CBS 139099; or
   ii. a combination of *Streptococcus thermophilus* and *Lactobacillus delbrueckii* subsp. *bulgaricus* microbial strains which together, or individually, are capable of secreting polysaccharides having high levels of galactosamine and no or low levels of rhamnose and glucuronic acid when grown on a dairy substrate,
so as to form a fermented dairy substrate;
b) providing two or more of the following components: a microbiome modifying component; a satiety modifying component; and a metabolic modifying component and mixing them together so as to form a mixture; and
c) forming the dairy product by:
   i) dispersing the mixture as a dispersion throughout the fermented dairy substrate;
   ii) mixing the mixture throughout the fermented dairy substrate; or
   iii) placing the mixture adjacently to the fermented dairy substrate.

Step b) may further comprise providing a probiotic culture in the fermented dairy substrate and/or mixture. The satiety modifying component may comprise glucomannan; the microbiome modifying component may comprise a prebiotic selected from: inulin, fructooligosaccharides (FOS), galactooligosaccharides (GOS), α-gluco-oligosaccharides, a low gas producing prebiotic and combinations thereof, and the metabolic modifying component may comprise chromium.

Preferably, the above methods comprise providing a microbiome modifying component; a satiety modifying component; and a metabolic modifying component.

The dairy product produced by the method may comprise one of the following: yoghurt, cheese, crème fraiche, sour cream, buttermilk, kefir, *acidophilus* milk, koumiss, filmjölk and viili. The dairy products may comprise a yoghurt. Due to the superior gel-like properties of the microbial strains and/or their secreted exopolysaccharides, the fermented dairy foodstuff may be a low fat product. The term "low fat" is intended to mean that the fat content of the fermented dairy foodstuff is lower than the standard foodstuff. Typically, "low fat" refers to foodstuffs having around 3 g or less of fat per 100 g of solid food or 1.5 g or less of fat per 100 ml of liquid food (according to the Food Standards Agency). Of course, "low fat" will also encompass lower fat variants of very high fat foodstuffs which may have higher fat contents than stipulated in the regulatory definition of "low fat". The fermented dairy foodstuff may increase satiation in an individual.

It will of course be apparent to the skilled addressee that the methods of producing a composition as herein above described may be employed to produce any of the compositions (and variations thereof) as outlined and described in the compositional aspects of the invention. Furthermore, additional steps may be incorporated into the methods such as formulation steps or steps incorporating the compositions into foodstuffs. In accordance with yet a further aspect of the present invention, there is provided a method of treating or managing obesity, elevated cholesterol, diabetes, hypertension or heart disease comprising administering a composition as herein above described in a therapeutically effective amount.

In accordance with another aspect of the present invention, there is provided a use of a composition as herein above, in the manufacture of a medicament for the treatment of obesity, elevated cholesterol, diabetes, hypertension or heart disease.

DETAILED DESCRIPTION OF THE INVENTION

Embodiments of the present invention will now be described, by way of example only with reference to the figures and examples detailed below.

Initial stages of developing the composition of the present invention focused on screening a large number of possible components to establish which components have a proven effect in weight management and which may be useful in combining with other components so as to provide a synergistic effect or combined modes of action. These components were also screened for toxicology profiles and whether they have been proved safe for human consumption.

Chromium

Chromium is a trace element that exists in foods and supplements in the trivalent form. Chromium levels are low in many staple foods; the better sources are processed meats, pulses, spices and whole grains. It plays a role in the metabolism of carbohydrate and fat and has attracted interest as a supplement that may promote weight loss.

Pittler et al. (2003) conducted the first meta-analysis of RCTs (10 trials, n=489) of chromium picolinate and weight loss. They reported a weighted mean difference of 1.1 kg (95% CI 1.8, 0.4) in favour of chromium picolinate over placebo.

Very recently, Onakpoya et al. (2013) conducted a meta-analysis on the effect of chromium supplementation on weight loss in overweight and obese adults. Their analysis of 11 RCT (n=866) reported a modest but statistically significant mean difference in weight of −0.5 kg (95% CI −0.96, −0.03) in favour of chromium over placebo. They also found a modest reduction in percentage body fat, but no effect on BMI or waist to hip circumference. The dose of chromium administered in the studies ranged from 137 µg/d to 1000 µg/d, but there was no clear evidence of a dose-response. Consequently, the authors noted it was difficult to determine a minimum effective dose, but reported that the largest weight loss tended to be found in RCTs with dosages of 400 µg/d.

Chromium has been suggested to improve insulin sensitivity, increase metabolic rate and reduce food cravings (Anderson 1998; Attenburrow et al. 2002; Onakpoya et al. 2013).

Onakpoya et al. (2013) reported some adverse effects in participants, including watery stools, vertigo, weakness, nausea, vomiting, dizziness and headaches. These adverse effects disappeared on withdrawal of chromium and reappeared when it was reintroduced. Other authors have reported constipation, decreased appetite and urticaria (Yazaki et al. 2010; Krol et al. 2011).

There is no reference nutrient intake for chromium, but COMA recommends that an intake above 25 µg/d is adequate for adults (DoH, 1991). The UK Food Standards Agency advise that intake up to 1000 µg/d from foods and/or supplements is likely to be safe.

There seems to be little data on the sensory effects of adding chromium to foods. Achanta et al. (2007) explored the effects of adding various minerals including chromium to yoghurts. They reported that addition of chromium at a level equivalent to 25% of the US RDA had no effect on the flavour or taste of yoghurt.

Glucomannan

Glucomannan is a soluble fibre derived from the perennial plant, *Amorphophallus konjac*. It consists of D-mannose and D-glucose in a molar ratio of 1.6:1.0, connected by $\beta(1,4)$-glycosidic bonds. Glucomannan has been attributed with a range of beneficial effects on parameters of obesity and cardiovascular risk (Doi 1995).

A fairly recent meta-analysis of 9 randomised controlled trials (RCT; n=379) reported that glucomannan causes a small, but statistically significant 0.79 kg (95% CI −1.53, −0.05) weight loss in trials averaging 5.2 weeks in duration (Sood et al. 2008). Weight loss was greatest in obese subjects (mean −1.30 (−1.69, −0.91) kg) and in RCTs with a parallel study design. The dose of glucomannan used in the studies ranged from 1.24 g/d to 15.1 g/d, the lower doses being supplied as capsules or tablets and the higher doses incorporated into granola bars or biscuits. Interestingly, the 3 studies that supplied glucomannan in biscuits or granola bars failed to report any significant weight change (Vuskan et al. 1999; Vuskan et al. 2000; Yoshida et al. 2006).

Salas-Salvado et al. (2008) conducted a 4 arm parallel design RCT to investigate the effects of a mixed fibre supplement (1 g glucomannan and 3 g *Plantago ovato* husk taken twice or three times daily) in the context of an energy-restricted diet on weight loss and metabolic variables in obese and overweight subjects. The study was designed with weight loss as the primary end point and was adequately powered to detect a modest 1.5 kg greater weight loss in the treatment groups. It was also of longer duration (16 weeks). At the end of the study the two fibres groups had lost marginally more weight (−4.52 (SD 0.56) and −4.60 (SD 0.58) kg) than the placebo group (−3.79 (SD 0.58) kg), but the difference between groups was not significant (P=0.43). The authors concluded that when taken in combination with an energy-restricted diet, a *Plantago ovato* and glucomannan fibre supplement has no additional benefit in promoting weight loss. The study did, however, demonstrate a favourable reduction in LDL cholesterol with both doses of fibre.

Glucomannan forms a viscous gel on exposure to an aqueous environment. Its gelling properties probably account for any weight loss promoting effects by delaying gastric emptying, slowing bowel transit time and blunting post-prandial surges in insulin and glucose (Chua et al. 2010). It is possible that glucomannan may also exert effects in the large bowel that could influence appetite and weight loss. Chen and associates reported that supplementation with 4.5 g/d of glucomannan for 21 d increased SOFA fatty acid concentrations and the proportion of lactobacilli and bifidobacteria in the faeces of healthy and constipated adults (Chen et al. 2006; Chen et al. 2008).

Glucomannan as Konjac flour has a long history of incorporation into foods in the Far East. Limited data from toxicological and genotoxicity studies indicate that glucomannon is safe (Oketani et al. 1991; Nihon Bioresearch Inc. 1992).

A number of researchers have added glucomannan to biscuits or granola bars (Vuksan et al. 1999 & 2000; Yoshida et al. 2006). Weight loss supplements need to contain 1 g of glucomannan per portion rather than the 3.3 g that Yoshida et al. (2006) incorporated into each of their bars. It is possible that 1 g will have less effect on the sensory properties of a food product than 3 g. Glucomannan has been used widely as an emulsifier, stabiliser and fat replacer which indicates that it can be successfully incorporated into foods (Chua et al. 2010).

Glucomannan is approved by EFSA for weight loss (EC, 2013) and a supplement needs to contain 1 g of glucomannan per quantified portion and consumers need to be informed that a beneficial effect is obtained with a daily intake of 3×1 g doses taken with water before meals in the context of an energy-restricted diet (EC 2013). It is also approved for a claim that it helps in the maintenance of normal blood cholesterol concentrations.

Prebiotics

A small number of studies have investigated whether acute treatment with prebiotics influences appetite and food intake. An early study by Archer et al. (2004) investigated the acute effect of inulin and lupin kernel fibre on fat intake, total energy intake and ratings of satiety over a 24 hour period. Using a 3 way cross-over design they fed participants (33 males, mean age 52 y, BMI 27.4 (SD 4.1)) a full-fat sausage patty and reduced-fat patties, with 50% of the fat replaced with inulin or lupin kernel for breakfast. The inulin containing patty led to a lower total fat intake and total energy intake on the test day, but had no effect on measures of satiety in comparison with the full fat patty. The patty containing lupin kernel fibre produced similar results, but also increased satiety for up to 5 h post breakfast. Peters et al. (2009) examined the acute effects of cereal bars enriched with inulin, β-glucan or a combination of inulin and β-glucan on food intake and 6 subjective ratings of hunger over a 2 day test period. They found no difference in energy intake or any of the 6 subjective ratings of hunger between treatments. In a 3 way cross-over study, Hess et al. (2011) fed participants two separate doses of 0, 5 and 8 g of short chain FOS (scFOS). On each test day, the first dose was incorporated into a hot cocoa beverage and consumed alongside breakfast. The second dose was incorporated into 3 chocolate-flavoured chews and consumed 2 h before dinner. The scFOS treatments failed to alter measures of satiety at breakfast or lunch and food intake during an ad libitum lunch. Over the remainder of the day, energy intake was significantly lower for women consuming the 16 g dose.

Only a few studies seem to have reported whether chronic supplementation with prebiotics influences adiposity in humans (Abrams et al. 2007; Parnell & Reimer 2009; Genta et al. 2009). Body mass index (BMI) increases during adolescence, with a healthy annual increment thought to be between 0.6-0.8 kg/m2 (Maynard et al. 2001). In a randomised placebo controlled trial, supplementation with FOS (8 g/d) for 12 months contributed to the maintenance of an appropriate BMI during pubertal growth (↑ 0.7 kg/m2 v ↑1.2 k/m2 over 12 months; n=97). This effect was modulated by habitual intake of dietary calcium, with prebiotic supplementation exhibiting more benefit in adolescents with a dietary calcium intake ≥700 mg/d (Abrams et al. 2007). In overweight or obese adults (BMI>25 kg/m2; n=48) a 3 month intervention with 21 g/d of FOS elicited a small but significant weight loss relative to a maltodextrin control (−1.03 (SD 0.43) kg v+0.45 (SD 0.31) kg; Parnell & Reimer 2009). In a study of obese pre-menopausal women (n=35) with slight dyslipidaemia, supplementation with yacon syrup (providing 10 g/d of FOS) for 120 d resulted in a remarkably large loss of weight (approx. 15 kg) and associated substantial reductions in BMI and waist circumference (Genta et al. 2009).

Using a randomised, single-blind, placebo-controlled, cross-over design, Cani et al. (2006) compared the effect of consuming FOS with a maltodextrin placebo (16 g/d×2 wk) on total energy intake and subjective ratings of appetite. At the end of each supplementation period, participants consumed a free-choice buffet meal for breakfast, lunch and dinner and rated their satiety, fullness, hunger and prospective food intake on visual analogue scales. FOS treatment significantly increased satiety at breakfast and dinner, increased fullness at dinner and decreased prospective food intake at dinner. Also, FOS treatment elicited a modest 5% reduction in total energy intake over a 24 hour test period. Using a similar experimental design, Cani et al. (2009) reported minor transient increases in the release of anorexic gut peptides (GLP-1 & PYY) in response to a test meal after 2 weeks of FOS supplementation relative to a maltodextrin placebo. An increase in anorexigenic and/or decrease in orexigenic gut peptides have been demonstrated in a few other studies (Parnell & Reimer, 2009; Tarini & Wolever 2010; Verhoef et al. 2011).

Recently, Harrold et al. (2013) conducted a placebo-controlled randomised cross-over study to compare the acute effects of a herbal product (Natural Remedies, UK) and a commercial inulin supplement (Fibresure; Proctor & Gamble) alone or in combination on appetite and food intake (58 normal to slightly overweight women). The herbal product contained Yerbe Mate, Guarana and Damiana (YGD). Both YGD and inulin induced a decrease in food intake and energy intake at an ad libitum lunch 4 h 15 min after administration, although the effect for YGD was greater than that for inulin (132.2 kcal v 89.84 kcal). These effects were enhanced when YGD and inulin were combined. The combination also elicited a significant decrease in hunger and the desire to eat. Studies combining inulin/FOS with other dietary fibres are limited. As described earlier Peters et al. (2009) explored possible synergies between inulin and β-glucans on food intake and ratings of hunger, but found no effect of either supplement alone or in combination.

The mechanism(s) through which prebiotics reduce food intake remain to be fully clarified, but the modulation of gut hormones may be important. Animal and human studies have reported increased release of the anorexigenic gut hormones, GLP-1 and PYY and inhibition of the orexigenic gut hormone, ghrelin in response to feeding inulin or FOS (Cani et al. 2004; Delzenne et al. 2005; Cani et al. 2009; Parnell & Reimer 2009; Tarini & Wolever 2010; Verhoef et al. 2011). These effects seem to be at least in part driven by short chain fatty acids produced from the colonic fermentation of prebiotics. GLP-1 and PYY are co-secreted from enteroendocrine L cells present in the intestinal epithelium (Habib et al. 2013). L cells contain receptors for SOFA and several experimental studies have demonstrated that infusion of SOFA into the colon induces the release of GLP-1 from colonic L cells (Cani et al. 2007). The mechanism(s) through which prebiotics may suppress the release of ghrelin are unclear, although it could be through altering the rate of nutrient absorption or the osmolality of the intestinal lumen (Overduin et al, 2005). If the effects of prebiotics on appetite are driven solely by SOFA rather than an increase in bifidobacteria, then similar effects may be expected from the consumption of resistant starch and soluble fibres.

Inulin is commonly used in the food industry in products such as ice cream, yoghurt and margarine as a fat replacer with the aim of reducing energy content. Devereux et al (2003) explored the sensory effects of adding inulin and FOS (range 4-13 g/100 g) to a range of other foodstuffs including bakery and meat products. All products were rated as acceptable by an untrained sensory panel, although most products were rated lower than their full-fat counterparts because of changes in texture and taste.

In addition to sensory acceptability it is important to consider whether food processing is likely to destroy the prebiotic activity of inulin and FOS. Huebner et al. (2008) explored the effect of pH, heat and Maillard reaction conditions on the prebiotic activity of FOS and inulin. Prebiotic activity was reduced by heating at low pH, but stable when subjected to low pH alone or Maillard reaction conditions. Bohm et al. (2005) reported that heating at high temperatures for 60 min caused substantial degradation of inulin to form di-D-fructose dianhydrides. These limited data indicate that it is important to quantify the amount of prebiotic in the final food product and/or measure its functional properties.

Carabin and Flamm (1999) reviewed the toxicological data from animal studies and adverse effect reports from clinical trials of inulin and FOS. They concluded that there is no evidence of treatment-related toxicity, genotoxicity or carcinogenicity. Furthermore, they failed to find evidence of detrimental effects on mineral absorption, lipid metabolism or glycaemic control. Adverse effects were limited to the GI tract, namely bloating, flatulence and diarrhoea, with effects becoming evident with single doses>20 g/d. Minor GI related adverse effects have been reported in most interventions with prebiotics, so there is interest in other potentially prebiotic oligosaccharides that may produce less gas. A commercial α-glucooligosaccharide (BioEcolians; Solibia) has been shown to produce less gas than inulin when fermented in a pH-controlled faecal batch culture, so could be a good candidate for inclusion in a weight loss product once its efficacy has been demonstrated (Sarbini et al. 2013).

Some FOS and inulin based weight loss supplements are on the market. For example, e'lefexir Flat Tummy Plus is a FOS based supplement sold to promote a flat tummy. Other products include Easyfibre® FOS, Jarrow Inulin FOS powder and USN Diet Fuel Ultra Lean. The latter product is a low GI meal replacement shake that contains a weight loss blend of FOS, calcium, N-acetyl-1-carnitine, hydroxycitric acid and fibre.

A further more detailed analysis of the literature based on efficacy of effect, likely effects on taste, safety/health effects and potential for synergy narrowed down this list of components to those identified in Table 1 below, it also identified an additional prebiotic of possible interest.

TABLE 1

| Dietary Fibre | Prebiotic | Mineral |
|---|---|---|
| Glucomannan (1 X 3 g/d) | FOS (5-7 g, 3 X d) Inulin (5-7 g, 3 X d) BioEolians (5-7 g, 3 X d) | Chromium (400 µg/d) |

Rationale for Using Glucomannan as the Base Ingredient:

The efficacy of glucomannan is supported by a meta-analysis of human trials that concluded that glucomannan promotes modest weight loss.

Rationale for Incorporation of Prebiotics in a Weight Loss Formulation:

There is evidence from human trials and substantial evidence from animal studies that prebiotics may favourably influence makers of appetite, food intake or weight loss. There is also some evidence of other beneficial metabolic and immunological effects that may complement any potential weight promoting/appetite suppressive effects. A side effect that is often reported in trials with fructan-based prebiotics is mild gastrointestinal distress/flatulence. Recently, a number of researchers have started to report that non-fructan based prebiotics produce less gas. The incorporation of one of these prebiotics such as α-gluco-oligosaccharides (BioEcolians, Soliba) or galactooligosaccharides (Vivinal GOS) into a product may prove beneficial.

Rationale for Incorporation of Chromium into a Weight Loss Formulation:

Two meta-analyses of human studies have concluded that supplementation with chromium promotes modest weight loss. Moreover, there is some evidence that chromium has other health benefits such as reducing fasting blood glucose concentrations and inflammation (Abdollahi et al. 2013; Chen et al. 2013).

Possibility of Synergy Between the Identified Components:

Chromium likely promotes weight loss by increasing insulin sensitivity and metabolic rate and perhaps through reducing food cravings. These effects seem to be mediated via signalling pathways that occur outside of the gastrointestinal tract. In contrast, the effects of glucomannan and prebiotics seem to relate to events occurring in the gut.

There has only been one study that investigating the effect of a supplement containing chromium and prebiotics (inulin) on weight loss in humans (Hoeger et al. 1998). In this study, a supplement combining chromium picolinate, inulin, *capsicum*, L-phenylalanine (an amino acid) and other poorly defined lipotropic nutrients caused a greater loss of body fat and maintenance of lean tissue than a placebo treatment in participants (n=123) following an aerobic exercise programme and energy restricted diet for 4 weeks (Hoeger et al. 1998).

One very recent study reported that a combination of glucomannan and chromium was effective at lowering total and LDL cholesterol in hypercholesterolaemic children whereas glucomannan alone was not, indicating that the components can act in synergy at least in relation to the control of blood cholesterol concentrations (Martino et al. 2013).

The screening suggested that glucomannan, prebiotics and chromium are the best likely candidates to include in a weight loss product. Studies reporting inhibition of appetite and/or weight loss after supplementation with prebiotics have administered 16-21 g/d in three equal doses, whereas beneficial effects of glucomannan have been reported at a daily intake of 3 g, and chromium may be effective at the µg level. The gram doses of glucomannan and prebiotics make it difficult to incorporate both into a weight loss capsule and suggest that a product combining the two would have to be a beverage or food. It is suggested that potential vehicles to explore are bread and other cereal/starchy products.

Average intakes of bread within the UK are approximately 2.5 medium slices of a large loaf per day (this equates to approximately 90 g) (Bates et al. 2011). Based on previous pilot work conducted in SHU, it seems feasible to incorporate prebiotics into bread at a concentration of approximately 8-10%. An average intake of bread would therefore provide approximately 50% of the recommended daily dose of prebiotics. So, it follows that any weight loss formulation would need to be incorporated into perhaps 2 or 3 food different food products that are commonly consumed throughout the day, e.g. breakfast cereals, bread, and another starchy staple such as pasta. It will also be necessary to explore the stability of glucomannan, prebiotics and chromium to the appropriate food processing techniques.

A weight loss food product should aim to supply 5-7 g of prebiotic, 1 g of glucomannan and 130 µg chromium per average portion.

EXAMPLES

The figures accompanying the below examples are as follows.

Experiments were conducted to prepare a weight management formulation in the form of yoghurt. Example 1A describes the formation of a base yoghurt which was then used to prepare a finished weight management yoghurt as outlined in Example 1B.

Example 1A—Initial Yoghurt Component

Yoghurts were prepared using the bacterial strains *Streptococcus thermophilus* (NIZO2274=Cell Deposit Ref: CBS 139100) and *Lactobacillus delbrueckii* subsp. *bulgaricus* (NIZO2118=Cell Deposit Ref: CBS 139099). Placebo yoghurts were also prepared using the bacterial strains *Streptococcus thermophilus* NIZO115 and *Lactobacillus delbrueckii* subsp. *bulgaricus* NIZO191; *Streptococcus thermophilus* NIZO131 and *Lactobacillus delbrueckii* subsp. *bulgaricus* NIZO191; and *Streptococcus thermophilus* NIZO131 and *Lactobacillus delbrueckii* subsp. *bulgaricus* NIZO194. The ingredients fermented by the bacterial cultures were 96.3% skimmed milk (w/w) and 3.7% cream (w/w). After formation of the yoghurts the pH and viscosity of the yoghurts was measured.

As shown in table 2 below yoghurts prepared using *Streptococcus thermophilus* NIZO2274 and *Lactobacillus delbrueckii* subsp. *bulgaricus* NIZO2118 had a greater viscosity than the placebo yoghurts. The yoghurts prepared using *Streptococcus thermophilus* NIZO2274 and *Lactobacillus delbrueckii* subsp. *bulgaricus* NIZO2118 also had a greater viscosity than yoghurts which included known thickening agents such as k-carrageenan, cekol (cellulose gum), guar (gum) and pectin.

TABLE 2

| Sample | Additive | pH after cultivation and cooling | Viscosity (sec postumus) |
| --- | --- | --- | --- |
| *S. therm* NIZO115 + *L. bulg.* NIZO191 | — | 4.15 | 7 |
| ISt concentrate | — | 4.24 | 14 |
| RR concentrate | — | 4.27 | 38 |
| *S. therm* NIZO131 + *L. bulg.* NIZO191 | — | 4.13 | 14 |
| *S. therm* NIZO131 + *L. bulg.* NIZO194 | — | 4.15 | 43 |
| *S. therm* NIZO2274 + *L. bulg.* NIZO2118 | — | 4.33 | 83 |

TABLE 2-continued

| Sample | Additive | pH after cultivation and cooling | Viscosity (sec postumus) |
| --- | --- | --- | --- |
| *S. therm* NIZO131 + *L. bulg.* NIZO194 | 0.1% K-car | 4.28 | 19 |
| *S. therm* NIZO131 + *L. bulg.* NIZO194 | 0.25% cekol | 4.28 | 13 |
| *S. therm* NIZO131 + *L. bulg.* NIZO194 | 0.25% guar | 4.27 | 11 |
| *S. therm* NIZO131 + *L. bulg.* NIZO194 | 0.25% pectin | 4.16 | 46 |
| *S. therm* NIZO115 + *L. bulg.* NIZO191 | — | 4.15 | 6 (6/6) |
| RR concentrate | — | 4.24 | 47 (48/46) |
| *S. therm* NIZO131 + *L. bulg.* NIZO191 | — | 4.14 | 19 (18/19) |
| *S. therm* NIZO131 + *L. bulg.* NIZO194 | — | 4.28 | 55 (55/54) |
| *S. therm* NIZO2274 + *L. bulg.* NIZO2118 | — | 4.42 | 69 (69/68) |
| *S. therm* NIZO131 + *L. bulg.* NIZO194 | 0.25% pectin | 4.26 | 30 (30/30) |

As shown in table 3 after 5 days storage at 4° C. the yoghurt prepared using *Streptococcus thermophilus* NIZO2274 and *Lactobacillus delbrueckii* subsp. *bulgaricus* NIZO2118 had a greater viscosity than the placebo yoghurt. The placebo yoghurt also had a coarse texture whereas the yoghurt prepared using *Streptococcus thermophilus* NIZO2274 and *Lactobacillus delbrueckii* subsp. *bulgaricus* NIZO2118 had a smooth texture.

TABLE 3

| Yoghurt | Viscosity (sec postumus) (20° C.) | pH | Structure |
| --- | --- | --- | --- |
| *S. therm* NIZO2274 + *L. bulg.* NIZO2118 | 77 | 4.30 | Smooth |
| *S. therm* NIZO115 + *L. bulg.* NIZO191 | 7 | 4.01 | Coarse, with pieces |

The exopolysaccharides secreted by the placebo culture *Streptococcus thermophilus* NIZO115 and *Lactobacillus delbrueckii* subsp. *bulgaricus* NIZO191 and by strains *Streptococcus thermophilus* NIZO2274 and *Lactobacillus delbrueckii* subsp. *bulgaricus* NIZO2118 were characterised. The placebo yoghurt prepared using strains *Streptococcus thermophilus* NIZO115 and *Lactobacillus delbrueckii* subsp. *bulgaricus* NIZO191 was labelled Yoghurt 14b, SATIN 1A. The yoghurt prepared using *Streptococcus thermophilus* NIZO2274 and *Lactobacillus delbrueckii* subsp. *bulgaricus* NIZO2118 was labelled Yoghurt 16, SATIN 5A. Tables 4, 5 and 6 below show the exopolysaccharide amounts, percentages and ratios in the yoghurts.

Tables 4, 5 and 6 show the differences in the complements of exopolysaccharides secreted by the different bacterial strains. Yoghurt 16 comprises a greater amount of galactosamine, galactose and glucose than yoghurt 14b. Yoghurt 14b comprises more rhamnose, mannose and glucuronic acid than yoghurt 16.

TABLE 4

| Sample Name | Begin Peak [min] | End Peak [min] | Amount Rhamnose ED_1 [mg/g EPS] | Amount Galactosamine ED_1 [mg/g EPS] | Amount Arabinose ED_1 [mg/g EPS] | Amount Glucosamine ED_1 [mg/g EPS] | Amount Galactose ED_1 [mg/g EPS] | Amount Glucose ED_1 [mg/g EPS] |
|---|---|---|---|---|---|---|---|---|
| A10, AH, Yoghurt 14b, SATIN 1A, fraction 3 | 25.0 | 27.0 | 197 | 0 | 0 | 0 | 15 | 171 |
| A11, AH, Yoghurt 16, SATIN 5A, fraction 3 | 25.0 | 27.0 | 0 | 166 | 0 | 0 | 402 | 200 |

| Sample Name | Amount Mannose ED_1 [mg/g EPS] | Amount Xylose ED_1 [mg/g EPS] | Amount Galacturonic acid ED_1 [mg/g EPS] | Amount Glucuronic acid ED_1 [mg/g EPS] | Total monosacch. ED_1 [mg/g EPS] |
|---|---|---|---|---|---|
| A10, AH, Yoghurt 14b, SATIN 1A, fraction 3 | 65 | 0 | 0 | 85 | 533 |
| A11, AH, Yoghurt 16, SATIN 5A, fraction 3 | 4 | 0 | 0 | 0 | 771 |

TABLE 5

| Sample Name | Begin Peak [min] | End Peak [min] | Amount Rhamnose ED_1 [%] | Amount Galactosamine ED_1 [%] | Amount Arabinose ED_1 [%] | Amount Glucosamine ED_1 [%] | Amount Galactose ED_1 [%] |
|---|---|---|---|---|---|---|---|
| A10, AH, Yoghurt 14b, SATIN 1A, fraction 3 | 25.0 | 27.0 | 37 | 0 | 0 | 0 | 2.7 |
| A11, AH, Yoghurt 16, SATIN 5A, fraction 3 | 25.0 | 27.0 | 0 | 21.5 | 0 | 0 | 52.1 |

| Sample Name | Amount Glucose ED_1 [%] | Amount Mannose ED_1 [%] | Amount Xylose ED_1 [%] | Amount Galacturonic acid ED_1 [%] | Amount Glucuronic acid ED_1 [%] | Total monosacch. ED_1 [%] |
|---|---|---|---|---|---|---|
| A10, AH, Yoghurt 14b, SATIN 1A, fraction 3 | 32.1 | 12.2 | 0 | 0 | 16 | 100 |
| A11, AH, Yoghurt 16, SATIN 5A, fraction 3 | 25.9 | 0.5 | 0 | 0 | 0 | 100 |

TABLE 6

| Sample Name | Begin Peak [min] | End Peak [min] | Amount Rhamnose ED_1 [ratio] | Amount Galactosamine ED_1 [ratio] | Amount Arabinose ED_1 [ratio] | Amount Glucosamine ED_1 [ratio] | Amount Galactose ED_1 [ratio] |
|---|---|---|---|---|---|---|---|
| A10, AH, Yoghurt 14b, SATIN 1A, fraction 3 | 25.0 | 27.0 | 14 | 0 | 0 | 0 | 1 |
| A11, AH, Yoghurt 16, SATIN 5A, fraction 3 | 25.0 | 27.0 | 0 | 1 | 0 | 0 | 2 |

| Sample Name | Amount Glucose ED_1 [ratio] | Amount Mannose ED_1 [ratio] | Amount Xylose ED_1 [ratio] | Amount Galacturonic acid ED_1 [ratio] | Amount Glucuronic acid ED_1 [ratio] |
|---|---|---|---|---|---|
| A10, AH, Yoghurt 14b, SATIN 1A, fraction 3 | 12 | 4 | 0 | 0 | 6 |
| A11, AH, Yoghurt 16, SATIN 5A, fraction 3 | 1 | 0 | 0 | 0 | 0 |

Size exclusion chromatography with refractive index, UV (280 nm, protein, polyphenols), viscosity and multi angle laser light scattering (MALLS) detection was used to determine the concentration, molar mass (Mw), radius Rh(w) and intrinsic viscosity [n]w of yoghurts 14b and 16.

The columns used were TSK gel PWXL Guard+TSK gel G6000 PWXL+TSK gel G5000 PWXL. The eluent (mobile phase) was 100 mM sodium nitrate, $NaNO_3$, +0.02% sodium azide, $NaN_3$. The flow rate was 0.500 mL/min. The column temperature was 35° C. The temperature used for the determination of the laser scattering, viscosity and refractive index was 35° C. The injection volume was 200 µl. The freeze dried samples (0.05 g) were weighed into a 20 ml bottle. 2.0 ml of eluent was added to the bottle and the sample was stirred overnight (16 hours) at room temperature. An ultrasonic bath was not used as this would break down the exopolysaccharides. The solutions were centrifuged for 10 minutes at 20,000 g in a 2 ml centrifuge tube. The solution was then filtered using a 0.22 µm filter (Millex-GV, low protein binding Durapore, PVDF, Cat no.: SLGVX13NL (Millipore)). 200 µl of the filtrated supernatant was then injected into the size exclusion chromatography column. The runtime injector was 131 minutes. The detection of the refractive index can indicate dissolved substances, minerals, lactose, proteins, casein micelles and solids content.

Figure 1:
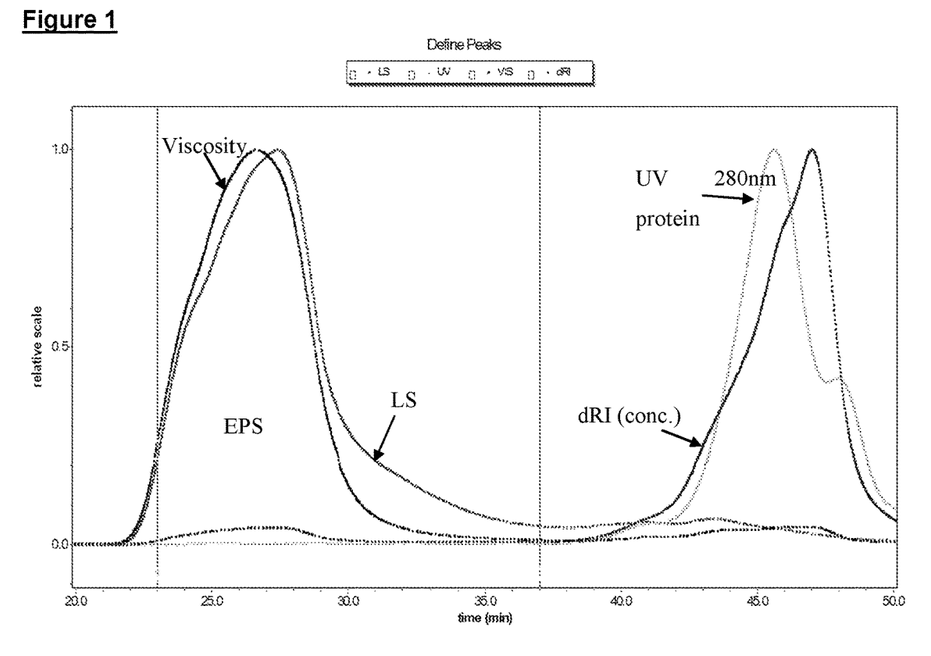
FIG. 1 is a graph showing the viscosity, laser scattering, UV absorption at 280 nm and differential refractive index of the exopolysaccharides of yoghurt 16.

FIG. 1 shows the viscosity, light scattering, refractive index and UV absorption at 280 nm of yoghurt 16.

Figure 2:
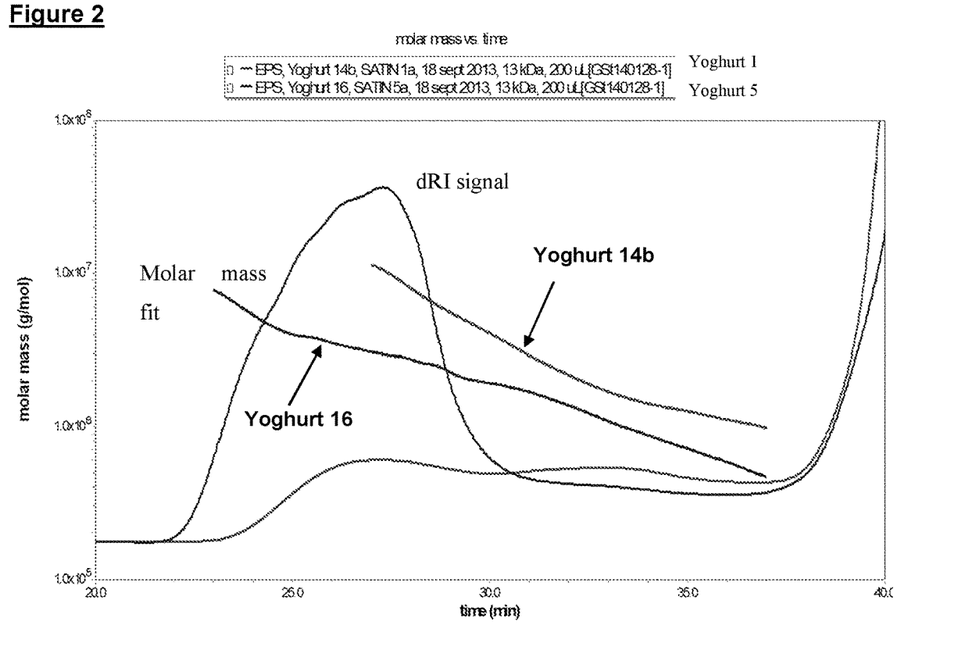
FIG. 2 is a graph showing molar mass plotted against time for yoghurts 14b and 16.
Figure 3:
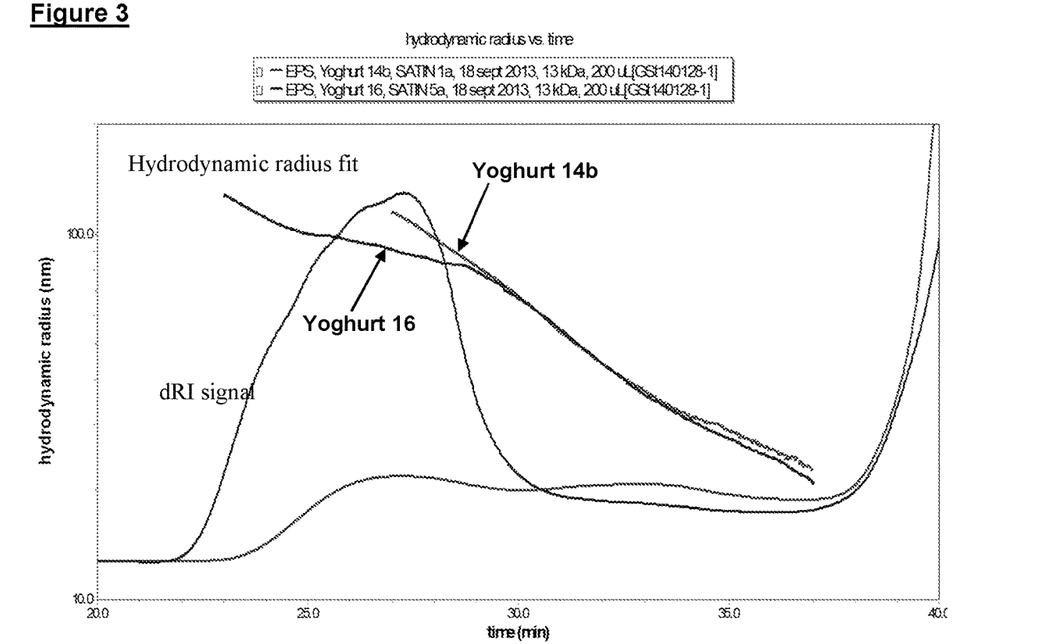
FIG. 3 is a graph showing hydrodynamic radius plotted against time for yoghurts 14b and 16.
Figure 4:
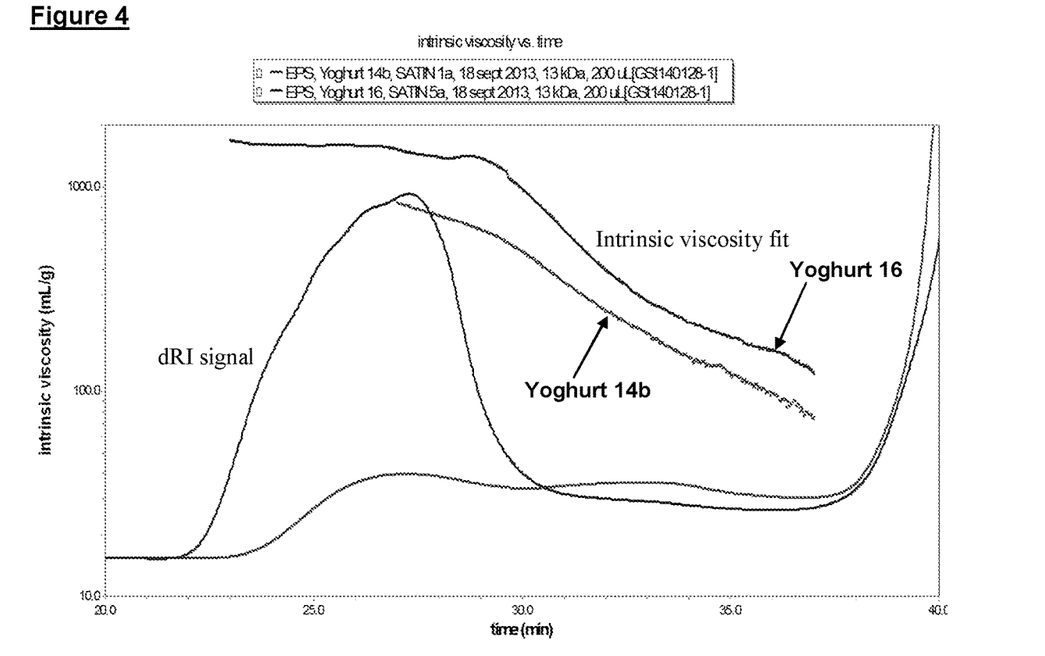
FIG. 4 is a graph showing intrinsic viscosity plotted against time for the yoghurts 14b and 16.

FIG. 2 shows yoghurt 16 has a greater molar mass compared to the placebo yoghurt 14b. FIG. 3 and table 9 show yoghurt 16 has a greater hydrodynamic radius compared to the placebo yoghurt 14b. FIG. 4 and table 9 show yoghurt 16 has a greater intrinsic viscosity than the placebo yoghurt 14b.

Figure 5:
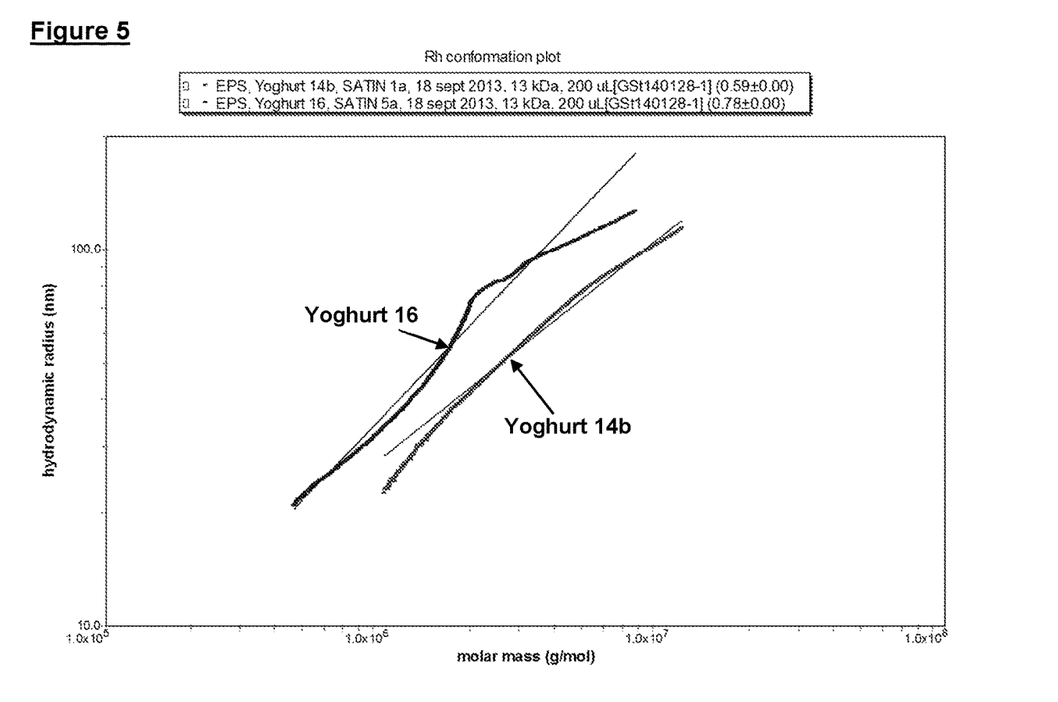
FIG. 5 is a graph showing an Rh conformation plot with hydrodynamic radius plotted against molar mass for yoghurts 14b and 16.

FIG. 5 shows the relationship between the hydrodynamic radius and molar mass for yoghurts 16 and 14b.

The figures show that yoghurt 16 prepared using strains *Streptococcus thermophilus* NIZO2274 and *Lactobacillus delbrueckii* subsp. *bulgaricus* NIZO2118 has a greater viscosity compared to the placebo yoghurt. These figures demonstrate that the amount and type of exopolysaccharides secreted by strains *Streptococcus thermophilus* NIZO2274 and *Lactobacillus delbrueckii* subsp. *bulgaricus* NIZO2118 produce a more viscous yoghurt.

Example 1B—Finished Yoghurt Product

A yoghurt product was prepared in order to investigate the potential of using a composition according to the invention in a weight management yoghurt product. In particular, the formulation, blending and organoleptic properties were investigated.

Three EFSA (European Food Safety Authority) approved ingredients, GOS prebiotic, glucomannan and chromium were added to a yoghurt produced via a common yoghurt protocol as outlined above in Example 1A using a unique combination of strains of *Streptococcus thermophilus* NIZO2274=NCIMB 700859=Cell Deposit Ref: CBS 139100) and *Lactobacillus delbrueckii* subsp. *bulgaricus* (NIZO2118=Cell Deposit Ref: CBS 139099) in order to assess product acceptability via a panel (n=4). Different formulations were tested and two types were considered acceptable in terms of taste, texture/consistency and mouth feel.

In the recipe, the yoghurt was prepared separately using the 2 strains: *Streptococcus thermophilus* and *Lactobaccillus bulgaricus* and the combination of these 2 strains led to a high viscosity yoghurt (69 sec posthumus).

To the standard ingredients, GOS prebiotic, glucomannan and chromium were added via the fruit. A serving size of 150 g was used which contained per serving size 6 g of prebiotic, 1 g of glucomannan, 130 µg chromium.

| Formulation | Standard g/100 g | GLU g/100 g | GLU/Chro/prebiotic g/100 g |
| --- | --- | --- | --- |
| yoghurt | 75 | 74 | 67 |
| sucrose | 5 | 5 | 5 |
| chromiumchloride 1% | — | — | 0.0087 |
| glucomannan | — | 0.67 | 0.67 |
| GOS 56% | — | — | 7.1 |
| fruitpreparation | 20 | 20 | 20 |

In these recipes, the same type of yoghurt was used. However, if desired, the protein and sucrose content of the yoghurt may be adjusted to optimise the protein and desired sweetness.

The yoghurt was prepared using the common yoghurt protocol. To the yoghurt a strawberry fruit preparation was added. In comparison to the standard recipe, GOS prebiotic, glucomannan and/or chromium were mixed with the strawberry fruit preparation with no issues. After mixing in the glucomannan, the strawberry fruit preparation became very viscous/thick within 30 min which was consequently used to prepare the fruited yoghurt in three ways after addition of the ingredients.

Direct mixing of the fruit preparation and yoghurt to a homogeneous product;

Directly adding the fruit preparation on the bottom to stiffen, before pouring the yoghurt on top; and Stiffening the strawberry preparation and gently mixing in the yoghurt to maintain pieces.

Figure 6:
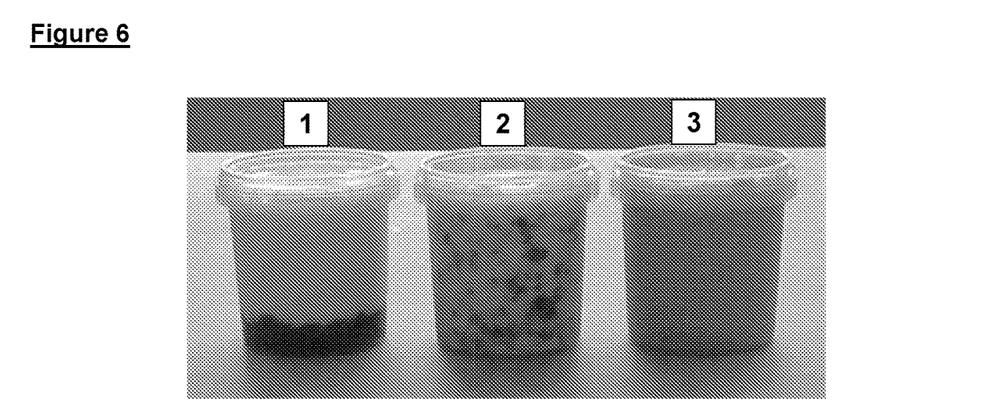
FIG. 6 shows photographs of three jars of yoghurt prepared according to the recipes outlined in the yoghurt Example A, in which (moving left to right) the yoghurt products produced were (1) fruit on the bottom, (2) fruit mixed in as pieces and (3) fruit mixed in homogeneous.

With reference to FIG. 6, three types of yoghurt were prepared and tested: (1) fruit on the bottom, (2) fruit mixed in as pieces and (3) fruit mixed in homogeneous. Upon a short organoleptic assessment of the product type by consumer type panel (n=4) the different preparations revealed different sensations:

(Type 1) The key effect of the addition of the glucomannan to the fruit was that although the visual impression was that it was a tough gel, it was actually very smooth, viscous and easy to smoothen in the mouth. Yoghurt flavour was recognizable.

(Type 2) The presence of fruit pieces (or on the bottom and mixed in with the yoghurt portion) provided a more fruity sensation of the product. Yoghurt flavour was recognizable.

(Type 3) The homogeneous product was evaluated as gluey like/sticky and coating the mouth with a less attractive flavour.

All yoghurt types had a thickness which was expected for a stirred yoghurt type. The sweetness of the yoghurt types differed. The yoghurt type 1 was regarded as less sweet compared to type 3.

The combination of GOS, glucomannan, chromium in the levels tested could produce an acceptable product when used by addition via a fruit preparation. The samples containing ingredients in the fruit preparation and provided as fruit on the bottom and/or as pieces in the product (type 1 and type 2) were considered the best and acceptable in terms of taste, texture/consistency and mouth feel.

Example 2—Worked Examples

The following yoghurt products are worked examples of yoghurts which may be produced in accordance with the present invention.

A yoghurt product may be produced in-line with that described with Example 1B "Finished Yoghurt Product" as detailed above. However, rather than adding all of the 'standard ingredients' (GOS prebiotic, glucomannan and chromium) via the fruit, only two of these ingredients are added to the yoghurt (either: GOS prebiotic+glucomannan; GOS prebiotic+chromium; or glucomannan and chromium).

Formulations for the worked examples are follows:

Formulation 2A

| Component | g/100 g |
|---|---|
| Yoghurt | 75 |
| Sucrose | 5 |
| Chromiumchloride 1% | 0.010 |
| GOS 56% | 10 |
| Fruit preparation | 20 |

Formulation 2B

| Component | g/100 g |
|---|---|
| Yoghurt | 75 |
| Sucrose | 5 |
| Glucomannan | 1.5 |
| GOS 56% | 9 |
| Fruit preparation | 20 |

Formulation 2C

| Component | g/100 g |
|---|---|
| Yoghurt | 75 |
| Sucrose | 5 |
| Chromiumchloride 1% | 0.0075 |
| Glucomannan | 1 |
| Fruit preparation | 20 |

As with Example 1B, if desired, the protein and sucrose content of the yoghurt may be adjusted to optimise the protein and desired sweetness.

The forgoing embodiments are not intended to limit the scope of the protection afforded by the claims, but rather to describe examples of how the invention may be put into practice.

Indications of Deposited Biological Material

A deposition of biological material by NIZO Food Research BV, of Kernhemseweg 2, 6718 ZB EDE, The Netherlands, was made at Centraalbureau voor Schimmelcultures, Uppsalalaan 8, P.O. Box 85167, 3508 AD UTRECHT, The Netherlands for the purposes of filing one or more patent applications. The Centraalbureau voor Schimmelcultures is a recognised International Depository Authority (IDA) under the Budapest Treaty and the deposition of biological material was made on the same terms as those laid down in the Treaty. Each of the strains deposited at the Centraalbureau voor Schimmelcultures have been assigned a number along with the prefix "CBS".

NIZO Food Research BV has authorised the Applicant to refer to the deposited biological material in this patent application and has provided their unreserved and irrevocable consent to the deposited material being made available to the public as from the date of filing of the patent application, including any subsequently filed patent application claiming priority therefrom.

The deposited biological referred to in this application is as follows:

Name: Centraalbureau voor Schimmelcultures
Address: Uppsalalaan 8
P.O. Box 85167
3508 AD UTRECHT
The Netherlands
Date: 25 Nov. 2014
Accession Number: CBS 139099
Description: *Lactobacillus delbrueckii* subsp. *bulgaricus*

—and—

Name: Centraalbureau voor Schimmelcultures
Address: Uppsalalaan 8
P.O. Box 85167
3508 AD UTRECHT
The Netherlands
Date: 25 Nov. 2014
Accession Number: CBS 139100
Description: *Streptococcus thermophilus*

LIST OF REFERENCES

Abdollahi M, Farshchi A, Nikfar S, Seyedifar M. Effect of chromium on glucose and lipid profiles in patients with type 2 diabetes; a meta-analysis review of randomized trials. J Pharm Pharm Sci. 2013; 16(1):99-114.

ABRAMS, S. A., GRIFFIN, I. J., HAWTHORNE, K. M. & ELLIS, K. J. 2007. Effect of prebiotic supplementation and calcium intake on body mass index. *J Pediatr*, 151, 293-8.

ACHANTA, K., ARYANA, K. J., BOENEKE, C. A. 2007. Fat free plain set yogurts fortified with various minerals. *Food Sci Tech*, 40, 424-429.

ANDERSON, R. A. 1998a. Chromium, glucose intolerance and diabetes. *J Am Coll Nutr*, 17, 548-55.

ANDERSON, R. A. 1998b. Effects of chromium on body composition and weight loss. *Nutr Rev*, 56, 266-70.

ARCHER, B. J., JOHNSON, S. K., DEVEREUX, H. M. & BAXTER, A. L. 2004. Effect of fat replacement by inulin or lupin-kernel fibre on sausage patty acceptability, post-meal perceptions of satiety and food intake in men. *Br J Nutr*, 91, 591-9.

ATTENBURROW, M. J., ODONTIADIS, J., MURRAY, B. J., COWEN, P. J. & FRANKLIN, M. 2002. Chromium treatment decreases the sensitivity of 5-HT2A receptors. *Psychopharmacology (Berl)*, 159, 432-6.

BATES B, LENNOX A, BATES C et al. (2011) National Diet and Nutrition Survey. Headline results from years 1 and 2 (combined) of the Rolling Programme (2008/2009-2009/10). Food Standards Agency & Department of Health, London.

BOHM, A., KAISER, I., TREBSTEIN, A. & HENLE, T. 2005. Heat-induced degradation of inulin. European Food Research and Technology, 220, 466-471.

CANI, P. D., JOLY, E., HORSMANS, Y. & DELZENNE, N. M. 2006. Oligofructose promotes satiety in healthy human: a pilot study. *Eur J Clin Nutr*, 60, 567-72.

CANI, P. D., HOSTE, S., GUIOT, Y. & DELZENNE, N. M. 2007. Dietary non-digestible carbohydrates promote L-cell differentiation in the proximal colon of rats. Br J Nutr, 98, 32-7.

CANI, P. D., LECOURT, E., DEWULF, E. M., SOHET, F. M., PACHIKIAN, B. D., NASLAIN, D., DE BACKER, F., NEYRINCK, A. M. & DELZENNE, N. M. 2009. Gut microbiota fermentation of prebiotics increases satietogenic and incretin gut peptide production with consequences for appetite sensation and glucose response after a meal. Am J Clin Nutr, 90, 1236-43.

CARABIN, I. G. & FLAMM, W. G. 1999. Evaluation of safety of inulin and oligofructose as dietary fiber. Regul Toxicol Pharmacol, 30, 268-82.

CHEN, H. L., CHENG, H. C., LIU, Y. J., LIU, S. Y. & WU, W. T. 2006. Konjac acts as a natural laxative by increasing stool bulk and improving colonic ecology in healthy adults. Nutrition, 22, 1112-9.

CHEN, H. L., CHENG, H. C., WU, W. T., LIU, Y. J. & LIU, S. Y. 2008. Supplementation of konjac glucomannan into a low-fiber Chinese diet promoted bowel movement and improved colonic ecology in constipated adults: a placebo-controlled, diet-controlled trial. J Am Coll Nutr, 27, 102-8.

CHUA, M., BALDWIN, T. C., HOCKING, T. J. & CHAN, K. 2010. Traditional uses and potential health benefits of Amorphophallus konjac K. Koch ex N.E.Br. J Ethnopharmacol, 128, 268-78.

DELZENNE, N. M., CANI, P. D., DAUBIOUL, C. & NEYRINCK, A. M. 2005. Impact of inulin and oligofructose on gastrointestinal peptides. Br J Nutr, 93 Suppl 1, S157-61.

DEVEREUX, H. M., JONES, G. P., McCORMACK, L., & HUNTER, W. C. 2003. Consumer acceptability of low fat foods containing inulin and oligofructose. J Food Sci, 68, 1850-1854.

DEPARTMENT OF HEALTH (1991): Dietary Reference Values for Food Energy and Nutrients for the United Kingdom. Report on Health and Social Subjects No. 41. HSMO, London DOI, K. 1995. Effect of konjac fibre (glucomannan) on glucose and lipids. Eur J Clin Nutr, 49 Suppl 3, S190-7.

GENTA, S., CABRERA, W., HABIB, N., PONS, J., CARILLO, I. M., GRAU, A. & SANCHEZ, S. 2009. Yacon syrup: beneficial effects on obesity and insulin resistance in humans. Clin Nutr, 28, 182-7.

HABIB, A. M., RICHARDS, P., ROGERS, G. J., REIMANN, F. & GRIBBLE, F. M. 2013. Co-localisation and secretion of glucagon-like peptide 1 and peptide YY from primary cultured human L cells. Diabetologia, 56, 1413-6.

HARROLD, J. A., HUGHES, G. M., O'SHIEL, K., QUINN, E., BOYLAND, E. J., WILLIAMS, N. J. & HALFORD, J. C. 2013. Acute effects of a herb extract formulation and inulin fibre on appetite, energy intake and food choice. Appetite, 62, 84-90.

HESS, J. R., BIRKETT, A. M., THOMAS, W. & SLAVIN, J. L. 2011. Effects of short-chain fructooligosaccharides on satiety responses in healthy men and women. Appetite, 56, 128-34.

Hoeger W W, Harris C, Long E M, Hopkins D R. Four-week supplementation with a natural dietary compound produces favorable changes in body composition. Adv. Ther. 1998 September-October; 15 (5):305-14.

HUEBNER, J., WEHLING, R. L., PARKHURST, A. & HUTKINS, R. W. 2008. Effect of processing conditions on the prebiotic activity of commercial prebiotics. International Dairy Journal, 18, 287-293.

KROL, E., KREJPCIO, Z., BYKS, H., BOGDANSKI, P. & PUPEK-MUSIALIK, D. 2011. Effects of chromium brewer's yeast supplementation on body mass, blood carbohydrates, and lipids and minerals in type 2 diabetic patients. Biol Trace Elem Res, 143, 726-37.

MARTINO, F., PUDDU, P. E., PANNARALE, G., COLANTONI, C., MARTINO, E., NIGLIO, T., ZANONI, C. & BARILLA, F. 2013. Low dose chromium-polynicotinate or policosanol is effective in hypercholesterolemic children only in combination with glucomannan. Atherosclerosis, 228, 198-202.

MAYNARD, L. M., WISEMANDLE, W., ROCHE, A. F., CHUMLEA, W. C., GUO, S. S. & SIERVOGEL, R. M. 2001. Childhood body composition in relation to body mass index. Pediatrics, 107, 344-50.

NIHON BIORESEARCH INC. HASHIMA LABORATORY, JAPAN. 1992. Study No. 823 1, Antigenicity Study of Propal A Using Bacteria OKETANI Y, ICHIKAWA K, ONO, C. 1991. Toxicity studies on glucomannan (1) acute toxicity in mice and rats. Journal of Applied Pharmacology, 27, 127-131.

ONAKPOYA, I., POSADZKI, P. & ERNST, E. 2013. Chromium supplementation in overweight and obesity: a systematic review and meta-analysis of randomized clinical trials. Obes Rev, 14, 496-507.

OVERDUIN, J., FRAYO, R. S., GRILL, H. J., KAPLAN, J. M. & CUMMINGS, D. E. 2005. Role of the duodenum and macronutrient type in ghrelin regulation. Endocrinology, 146, 845-50.

PARNELL, J. A. & REIMER, R. A. 2009. Weight loss during oligofructose supplementation is associated with decreased ghrelin and increased peptide YY in overweight and obese adults. Am J Clin Nutr, 89, 1751-9.

PETERS, H. P., BOERS, H. M., HADDEMAN, E., MELNIKOV, S. M. & QVYJT, F. 2009. No effect of added beta-glucan or of fructooligosaccharide on appetite or energy intake. Am J Clin Nutr, 89, 58-63.

PITTLER, M. H., STEVINSON, C. & ERNST, E. 2003. Chromium picolinate for reducing body weight: meta-analysis of randomized trials. Int J Obes Relat Metab Disord, 27, 522-9.

SALAS-SALVADO, J., FARRES, X., LUQUE, X., NAREJOS, S., BORRELL, M., BASORA, J., ANGUERA, A., TORRES, F., BULLO, M. & BALANZA, R. 2008. Effect of two doses of a mixture of soluble fibres on body weight and metabolic variables in overweight or obese patients: a randomised trial. Br J Nutr, 99, 1380-7.

SOOD, N., BAKER, W. L. & COLEMAN, C. I. 2008. Effect of glucomannan on plasma lipid and glucose concentrations, body weight, and blood pressure: systematic review and meta-analysis. Am J Clin Nutr, 88, 1167-75.

TARINI, J. & WOLEVER, T. M. 2010. The fermentable fibre inulin increases postprandial serum short-chain fatty acids and reduces free-fatty acids and ghrelin in healthy subjects. Appl Physiol Nutr Metab, 35, 9-16.

VERHOEF, S. P., MEYER, D. & WESTERTERP, K. R. 2011. Effects of oligofructose on appetite profile, glucagon-like peptide 1 and peptide YY3-36 concentrations and energy intake. Br J Nutr, 106, 1757-62.

VUKSAN, V., JENKINS, A. L., ROGOVIK, A. L., FAIRGRIEVE, C. D., JOVANOVSKI, E. & LEITER, L. A. 2011. Viscosity rather than quantity of dietary fibre predicts cholesterol-lowering effect in healthy individuals. Br J Nutr, 106, 1349-52.

VUKSAN, V., JENKINS, D. J., SPADAFORA, P., SIEVENPIPER, J. L., OWEN, R., VIDGEN, E., BRIGHENTI, F., JOSSE, R., LEITER, L. A. & BRUCE-THOMPSON, C. 1999. Konjac-mannan (glucomannan) improves glycemia and other associated risk factors for coronary heart disease in type 2 diabetes. A randomized controlled metabolic trial. *Diabetes Care,* 22, 913-9.

VUKSAN, V., SIEVENPIPER, J. L., OWEN, R., SWILLEY, J. A., SPADAFORA, P., JENKINS, D. J., VIDGEN, E., BRIGHENTI, F., JOSSE, R. G., LEITER, L. A., XU, Z. & NOVOKMET, R. 2000. Beneficial effects of viscous dietary fiber from Konjac-mannan in subjects with the insulin resistance syndrome: results of a controlled metabolic trial. *Diabetes Care,* 23, 9-14.

YAZAKI, Y., FARIDI, Z., MA, Y., ALI, A., NORTHRUP, V., NJIKE, V. Y., LIBERTI, L. & KATZ, D. L. 2010. A pilot study of chromium picolinate for weight loss. *J Altern Complement Med,* 16, 291-9.

YOSHIDA, M., VANSTONE, C. A., PARSONS, W. D., ZAWISTOWSKI, J. & JONES, P. J. 2006. Effect of plant sterols and glucomannan on lipids in individuals with and without type II diabetes. *Eur J Clin Nutr,* 60, 529-37

The invention claimed is:

1. A composition comprising:
    a) at least two of the following components:
       a microbiome modifying component;
       a satiety modifying component; and
       a metabolic modifying component,
    and
    b) at least one of following:
       i) *Streptococcus thermophilus* CBS 139100 and *Lactobacillus delbrueckii* subsp. *bulgaricus* CBS 139099; or
       ii) a combination of *Streptococcus thermophilus* CBS 139100 and *Lactobacillus delbrueckii* subsp. *bulgaricus* CBS 139099 microbial strains which secrete a combination of exopolysaccharides; comprising up to 25% galactosamine, up to 60% galactose and up to 30% glucose based on the total weight of secreted exopolysaccharides
       wherein said composition comprises:
          15%-25% galactosamine;
          45%-60% galactose; and
          20%-30% glucose.

2. The composition of claim 1, wherein the composition comprises 25% galactosamine.

3. The composition of claim 1, wherein the composition 45%-60% galactose, 20%-30% glucose and 25% galactosamine, based on the total weight of secreted exopolysaccharides.

4. The composition of claim 1, comprising b(i) *Streptococcus thermophilus* CBS 139100 and *Lactobacillus delbrueckii* subsp. *bulgaricus* CBS 139099 microbial strains.

5. The composition of claim 1 wherein the microbiome modifying component comprises one or more additional microbial strains.

6. The composition of claim 1, wherein the microbiome modifying component comprises a prebiotic; the satiety modifying component comprises dietary fibre and the metabolic modifying component comprises chromium.

7. The composition of claim 6, wherein the dietary fibre comprises glucomannan, and/or a prebiotic comprising inulin, fructooligosaccharides (FOS), galactooligosaccharides (GOS), α-gluco-oligosaccharides, a low gas producing prebiotic or a combination thereof.

8. A daily dosage form of the composition of claim 6 comprising the dietary fibre in a range of 0.5 g to 15 g, chromium in a range of 50 µg to 1000 µg, and prebiotic in a range of 3 g to 30 g.

9. The composition of claim 1 wherein the composition is grown on a dairy substrate, is formed as part of a dairy substrate or product, or is used as a feedstock, ingredient or additive for use with a fermented or fermentable dairy foodstuff.

10. The composition of claim 9, wherein the fermented or fermentable dairy foodstuff is yoghurt, cheese, crème fraiche, sour cream, buttermilk, kefir, *acidophilus* milk, koumiss, filmjölk or viili.

11. The composition of claim 9, wherein the composition farther comprises sweeteners, stabilisers, acidity regulators, water, flavourings, fats, emulsifiers, plant extracts, vegetable extracts, vitamins, minerals, phytochemicals, antioxidants, or combinations thereof.

12. The composition of claim 1, wherein the composition comprises:
    a) 50% to 90% fermented or fermentable dairy food stuff comprising and/or fermented using *Streptococcus thermophilus* CBS 139100 and *Lactobacillus delbrueckii* subsp. *bulgaricus* CBS 139099;
    b) 1% to 10% sweetener;
    c) 5% to 20% GOS;
    d) up to 1.5% glucomannan;
    e) up to 0.010% chromium chloride; and
    f) 5% to 30% fruit preparation.

13. A method for treatment or management of weight, obesity, elevated cholesterol, diabetes, hypertension or heart disease comprising providing the composition of claim 1 to a subject in need thereof.

14. A method of producing a composition comprising:
    A) providing two or more of the following components:
       a) a microbiome modifying component;
       b) a satiety modifying component;
       c) a metabolic modifying component
       and
       d) at least one of the following:
          i) *Streptococcus thermophilus* CBS 139100 and *Lactobacillus delbrueckii* subsp. *bulgaricus* CBS 139099 microbial strains or;
          ii) a combination of *Streptococcus thermophilus* CBS 139100 and *Lactobacillus delbrueckii* subsp. *bulgaricus* CBS 139099 microbial strains which together, or individually, are capable of secreting polysaccharides having high levels of galactosamine and no or low levels of rhamnose and glucuronic acid when grown on a dairy substrate; and
          iii) polysaccharides formed of:
             1) 15%-25% galactosamine;
             2) 45%-60% galactose; and
             3) 20%-30% glucose,
          and
    B) mixing the chosen components from a), b) and c) together with at least one of the chosen components of d), so as to form a mixture.

15. A method of producing a dairy product comprising the steps:
    a) fermenting an initial dairy substrate using a culture comprising:
       i) *Streptococcus thermophilus* CBS 139100 and *Lactobacillus delbrueckii* subsp. *bulgaricus* CBS 139099; or
       ii) a combination of *Streptococcus thermophilus* CBS 139100 and *Lactobacillus delbrueckii* subsp. *Bulgaricus* CBS 139099 microbial strains which together, or individually, are capable of secreting polysaccharides having high levels of galactosamine and no or low levels of rhamnose and glucuronic acid when grown on a dairy substrate,
so as to form a fermented dairy substrate;
b) providing two or more of the following components: a microbiome modifying component; a satiety modifying component; and a metabolic modifying component and mixing them together so as to form a mixture; and
c) forming the dairy product by:
  i) dispersing or suspending the mixture throughout the fermented dairy substrate;
  ii) mixing the mixture throughout the fermented dairy substrate; or
  iii) placing the mixture adjacently to the fermented dairy substrate.

16. The method of claim 15, wherein step b) further comprises providing or adding a probiotic culture to the fermented dairy substrate or mixture.

17. The method of claim 15, wherein the satiety modifying component comprises glucomannan; the microbiome modifying component comprises a prebiotic selected from: inulin, fructooligosaccharides (FOS), galactooligosaccharides (GOS), α-gluco-oligosaccharides, a low gas producing prebiotic or a combination thereof; and the metabolic modifying component comprises chromium.

18. The method of claim 15, wherein the method further comprises adding one or more ingredients selected from: sweeteners, stabilisers, acidity regulators, water, flavourings, fats, emulsifiers, plant extracts, vegetable extracts, vitamins, minerals, phytochemicals, antioxidants, or a combination thereof, and wherein the dairy product comprises one of the following: yoghurt, cheese, crème fraiche, sour cream, buttermilk, kefir, *acidophilus* milk, koumiss, filmjölk and viili.

* * * * *

UNITED STATES PATENT AND TRADEMARK OFFICE
CERTIFICATE OF CORRECTION

PATENT NO. : 10,645,965 B2  
APPLICATION NO. : 15/524739  
DATED : May 12, 2020  
INVENTOR(S) : Stephen Patrick O'Hara Page 1 of 1

It is certified that error appears in the above-identified patent and that said Letters Patent is hereby corrected as shown below:

In the Claims

Column 24, Line 43, (Claim 3), insert --comprises-- after "composition"

Signed and Sealed this  
Eighth Day of September, 2020

Andrei Iancu  
*Director of the United States Patent and Trademark Office*